(12) United States Patent
Powell et al.

(10) Patent No.: US 9,439,990 B2
(45) Date of Patent: Sep. 13, 2016

(54) LEAK-PROOF CONTACT LENS CONTAINER

(71) Applicant: Abbott Medical Optics Inc., Santa Ana, CA (US)

(72) Inventors: Charles Hayes Powell, Irvine, CA (US); Daniel John Urbaniak, Aliso Viejo, CA (US)

(73) Assignee: Abbott Medical Optics Inc., Santa Ana, CA (US)

(*) Notice: Subject to any disclaimer, the term of this patent is extended or adjusted under 35 U.S.C. 154(b) by 508 days.

(21) Appl. No.: 13/948,922

(22) Filed: Jul. 23, 2013

(65) Prior Publication Data

US 2015/0030511 A1    Jan. 29, 2015

(51) Int. Cl.
*A61L 2/18* (2006.01)
*A61L 12/12* (2006.01)

(52) U.S. Cl.
CPC ............... *A61L 2/18* (2013.01); *A61L 12/124* (2013.01)

(58) Field of Classification Search
CPC ........... A61L 2/18; A61L 2/186; A61L 2/26; A61L 12/086; A61L 12/124; A61L 12/126; A61L 12/128; A61L 2202/12; A61L 2202/121; A61L 2202/122; B32B 3/26; B32B 1/02
See application file for complete search history.

(56) References Cited

U.S. PATENT DOCUMENTS

| | | |
|---|---|---|
| 3,715,047 A | 2/1973 | Sado |
| 4,396,583 A | 8/1983 | LeBoeuf |
| 4,637,919 A | 1/1987 | Ryder et al. |
| 4,826,000 A | 5/1989 | Danker et al. |
| 5,176,271 A | 1/1993 | Painchaud et al. |
| 5,362,647 A | 11/1994 | Cook et al. |
| 5,521,091 A | 5/1996 | Cook et al. |
| 6,000,534 A | 12/1999 | Koomruian, Jr. |
| 6,274,209 B1 | 8/2001 | Pagidas et al. |
| 6,945,392 B2 * | 9/2005 | Furukawa .............. B65D 33/01 206/213.1 |
| 2009/0230078 A1 | 9/2009 | Walsh |

* cited by examiner

*Primary Examiner* — Timothy Cleveland
(74) *Attorney, Agent, or Firm* — Abbott Medical Optics Inc.

(57) ABSTRACT

A container for disinfecting and storing a contact lens comprising a container having a nonporous but oxygen-permeable, water-impermeable liner that forms a continuous barrier layer to allow oxygen to escape but prevent water from escaping when the container becomes pressurized, such as when an oxidative disinfectant is neutralized catalytically to generate free oxygen ($O_2$). A rigid shell against which the liner is disposed is porous to oxygen and includes a main body and a cap removably attachable to an upper rim of the main body. The container also may have a lens holder for supporting a contact lens. The liner may be on the inside of the shell, or vice versa. The liner may be on the inside of the cap which has openings through which the liner expands when the container becomes pressurized as an indicator that the disinfecting process is underway. The liner may be constructed of a nonporous silicone and the shell of polyethylene or other rigid plastic that can be constructed as a highly gas-porous enclosure.

18 Claims, 3 Drawing Sheets

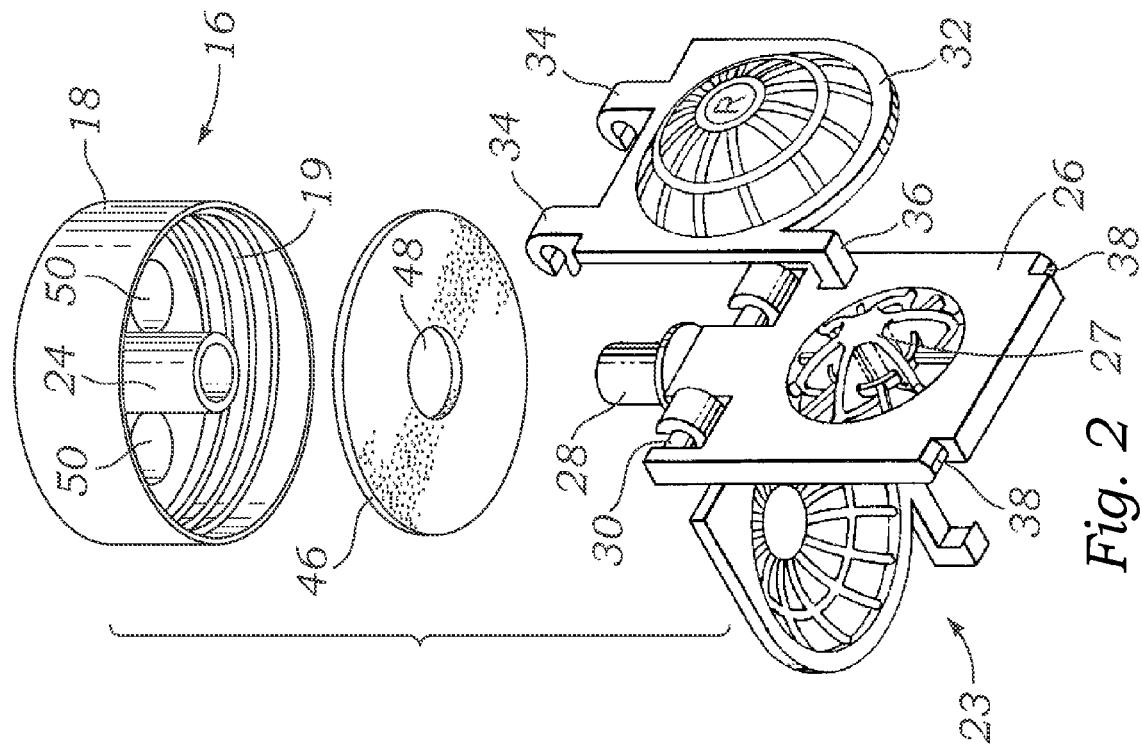
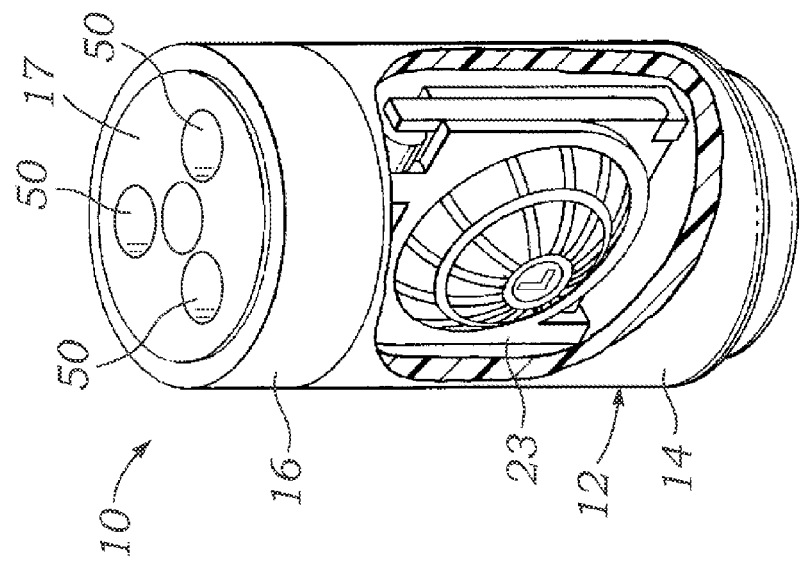

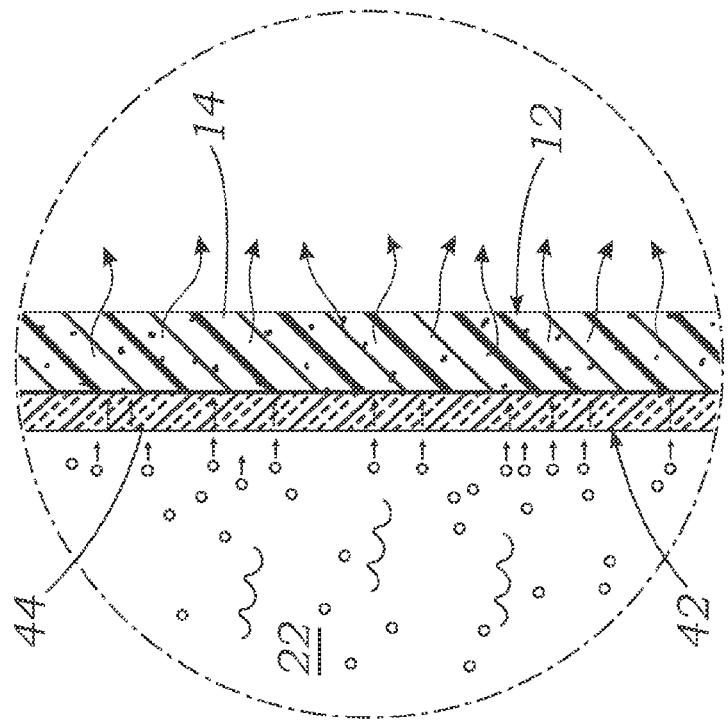
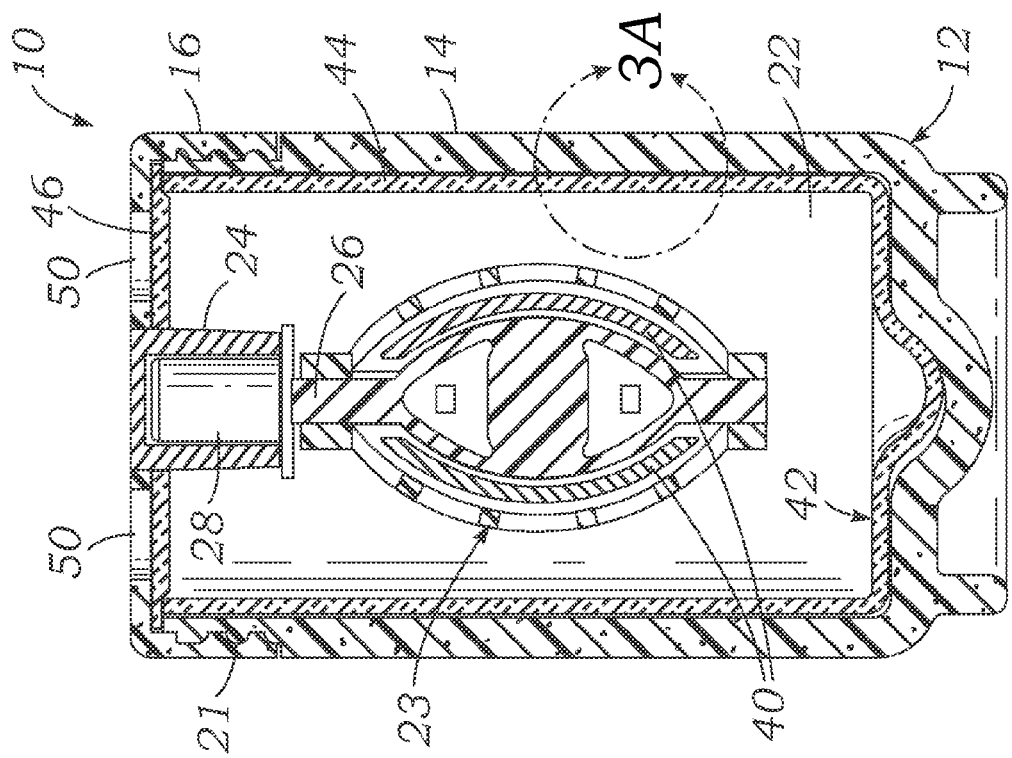

LEAK-PROOF CONTACT LENS CONTAINER

FIELD OF THE INVENTION

Containers for holding and disinfecting contact lenses, in particular that prevent water leakage where the disinfecting process creates pressure in the container.

BACKGROUND OF THE INVENTION

Use of hydrogen peroxide for the chemical sterilization or disinfecting of soft contact lenses is well-known in the art. Such lenses are generally disinfected inside particularly-crafted contact lens holders. Hydrogen peroxide is an oxidative disinfectant which, as part of the disinfection process, breaks down into water and oxygen. For such disinfection systems, the container holding the lenses and the disinfectant must be designed to allow oxygen to escape to prevent excess buildup of vapor pressure and potential explosion or rupture of the container.

For example, U.S. Pat. No. 4,637,919 discloses a lens disinfecting container with a filter cartridge for use with oxidative disinfectants. This allows oxygen produced by decomposing hydrogen peroxide to escape from the device. Other attempts to solve this problem include U.S. Pat. No. 4,396,583 where a gas-permeable, liquid-impermeable membrane is loosely fitted inside a space in a cap of the device. The membrane is positioned between the disinfecting chamber and apertures located in the cap. The apertures in the cap allow gas which has passed through the membrane to escape.

Unfortunately, neither the '583 patent nor the '919 patent adequately solve the problem of venting the oxygen created during hydrogen peroxide decomposition while providing a leak-proof and non-clogging container. The '919 patent provides a container with minimal surface area to allow oxygen to escape. In addition, leakage is a potential problem as the filter cartridge is not adequately secured inside the aperture into which it is placed. Moreover, the filter cartridge would have a tendency to clog because of its minimal surface area. The '583 patent is also inadequate because it provides a membrane which can be easily dislodged so that the container is likely to leak.

There remains a need for a contact lens disinfecting container with a gas-permeable, liquid-impermeable member fixed securely thereto which can properly and adequately vent oxygen created during hydrogen peroxide decomposition without clogging or leaking.

SUMMARY OF THE INVENTION

The present application provides a container for disinfecting and storing contact lenses including a main body defining within an inner space and having an open end, a lens holding means for supporting at least one contact lens within the inner space, a cap for sealably covering the open end of the main body, and a gas-permeable, liquid-impermeable liner disposed against the main body and cap to provide a continuous barrier layer surrounding the inner space when the cap attaches to the main body.

The present containers provide devices for disinfecting and storing a contact lens comprising a main body including an open end, a lens holding means for supporting at least one contact lens within the container, a cap for sealably covering the open end of the container wherein the cap having an internal and external surface, and an oxygen-permeable, water-impermeable liner secured to the inner or outer surfaces of the main body and cap.

The foregoing and other features and advantages of the invention will become more apparent from the following detailed description, which proceeds with reference to the accompanying figures.

BRIEF DESCRIPTION OF THE DRAWINGS

FIG. 1 is a perspective view of a disinfectant container for contact lenses as disclosed herein partially cutaway to show an internal basket assembly for supporting contact lenses within an inner space;

FIG. 2 is an exploded perspective of a cap of the container of FIG. 1 and the internal basket assembly;

FIG. 3 is a vertical sectional view through a midline of the container of FIG. 1 showing one embodiment of a leak-proof inner liner and rigid porous outer shell;

FIG. 3A is an enlarged view of one section of the container wall from FIG. 3 showing the leak-proof liner and porous shell and illustrating a transport mechanism for the escape of oxygen from the inner space to the exterior of the container;

DETAILED DESCRIPTION OF THE PREFERRED EMBODIMENTS

Figure 4:
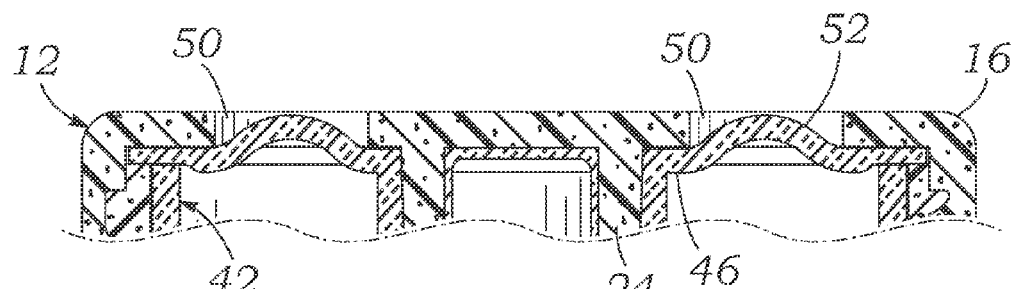
FIG. 4 is a detailed sectional view an upper end of the container of FIG. 3 showing an alternative configuration for the leak-proof liner.

The containers disclosed herein can be used with all contact lenses such as conventional hard, soft, rigid gas permeable, and silicone lenses. The container is preferably employed with soft lenses, such as those commonly referred to as hydrogel lenses. Hydrogel lenses are typically prepared from monomers, such as hydroxyethylmethacrylate, vinylpyrrolidone, glyceryl-methacrylate, methacrylic acid or acid esters and the like. Such hydrogel lenses include disposable, extended wear and continuous wear lenses.

The present containers provide receptacles for disinfecting and storing a contact lens in solution, in particular using oxidative disinfectant solutions which generate oxygen during the disinfectant process and thus increase the pressure within the containers. Particularly useful oxidative disinfectant components are hydrogen peroxide or one or more other peroxide-containing compounds. Precursors to chlorine dioxide, such as stabilized purite, are also effective. The containers disclosed herein are useful with any disinfectant or, for that matter, storage solution that generates oxygen during the disinfectant process or over time, thus necessitating some form of pressure release.

For hydrogen peroxide, a 0.5% (w/v) concentration, for example, in an aqueous liquid medium, is often effective as a disinfectant component. It is preferred to use at least about 1.0% or about 2.0% (w/v) hydrogen peroxide which concentrations reduce the disinfecting time over that of the 0.5% (w/v) peroxide concentration. No upper limit is placed on the amount of hydrogen peroxide which can be used with the present containers except as limited in that the oxidative disinfectant component should have no substantial detrimental effect on the contact lens being treated or on the eye of the wearer of the treated contact lens. An aqueous solution containing about 3% (w/v) hydrogen peroxide is very efficacious.

When an oxidative disinfectant is used in the present invention, preferably a reducing or neutralizing catalyst in an amount sufficient to chemically reduce or neutralize substantially all of the oxidative disinfectant, for example, hydrogen peroxide, is employed. Neutralizing components are well known to those of skill in the art and include catalytic elements such as platinum, as well as catalase. Preferably, a non-bovine derived form of catalase is utilized. Preferably, a catalase produced by *Aspergillus niger* or *Micrococcus luteus* is used. Use of such catalases is disclosed in U.S. Pat. Nos. 5,362,647 and 5,521,091.

FIGS. 1 and 2 illustrate a container 10 of the present application defined by a rigid shell 12 having a main body 14 and a cap 16. The cap 16 includes a flat circular top wall 17 and a circumferential side wall 18. As seen in the exploded view of FIG. 2 and also with reference to FIG. 3, internal threads 19 on the inside of the circumferential side wall 18 mate with external threads provided on an upper tubular lip 21 of the main body 14. When the cap 16 is screwed onto the main body 14, a closed inner space 22 (see FIG. 3) sized to receive one or more contact lenses is defined.

FIG. 1 illustrates a portion of the container 10 cut away to show a lens-holding basket assembly 23, which is seen in greater detail in FIG. 2.

FIG. 2 provides an exploded perspective of the cap 16 and internal basket assembly 23. The cap 16 includes a lens basket mounting plug 24 depending axially downward from a central point under the top wall 17 (FIG. 1). The lens-holding basket assembly 23 comprises a supporting frame 26 fixed below a frame stem 28 with horizontal shaft-like gudgeons 30 upon which opposed lens covers 32 are attached via snap-fittings 34. The opposed lens covers 32 can rotate upward and then downward on the gudgeons 30 to cover opposed convex lens receiving surfaces 27 on the supporting frame 26. Each lens cover 32 may be secured to the supporting frame 26 with a claw 36 which snaps over one of two lower bosses 38. Of course, this is just one example of a lens-holding basket, and the application incorporates many others.

FIG. 3 provides a cross-sectional view of the container 10 with contact lenses 40 held within two separate convex receptacles defined by the internal basket assembly 23. As mentioned, the container 10 includes a rigid shell 12 defined by the main body 14 having an open upper end, and the cap 16 screwed thereon. In addition to the rigid shell 12, a liner 42 is provided to prevent water leaking from the container. In the embodiment of FIG. 3, the liner 42 is intimately disposed against the inner surfaces of the rigid shell 12, and thus provides an inner liner. As will be explained below, however, the liner 42 may also be disposed only outside of the rigid shell 12.

Since the container 10 is formed in two parts, so is the rigid shell 12 and the liner 42. In particular, the liner 42 includes a first liner section 44 disposed against the inner surfaces of the main body 14 and a second liner section 46 against the inner surfaces of the cap 16. Both the first and second sections 44, 46 may be affixed to the respective inner wall surfaces with glue, welding, or the like, or may be coated thereon. When the cap 16 is screwed onto the main body 14, the first and second sections 44, 46 of the liner 42 come into intimate contact in such a manner as to ensure a continuous barrier layer of water-impermeable material surrounding the inner space 22. More particularly, the first liner section 44 includes a generally tubular side wall that extends up to an upper rim at the top edge of the upper tubular lip 21 of the main body 14, and both the first liner section 44 and the lip 21 come into direct contact with the wider second liner section 46 under the cap 16. Contact between the upper edge of the side wall 48 and underside of the second liner section 46 creates a small amount of compression which provides an adequate seal to prevent water from passing therebetween. This seal or seam between the first and second sections 44, 46 therefore ensures a continuous barrier layer of the material of the liner 42 around the inner space 22, except at the mounting plug 24.

To complete the continuous barrier layer of water-impermeable material surrounding the inner space 22, the lens basket mounting plug 24 is desirably made of a water-impermeable rigid material, in contrast to the rest of the rigid shell 12. The mounting plug 24 can easily be molded separately and then inserted into a close-fit aperture on the cap 16 and sealed therein with thermal welding, adhesives or the like. To simplify the container, the suspended lens-holding basket 23 may be replaced with one that merely fits closely within the inner space 22, thus eliminating the mounting plug 24. Embodiments of this configuration are shown and described herein.

The second liner section 46 disposed under the cap 16 is desirably an annular disc as seen in FIG. 2 having a central aperture 48 that receives the mounting plug 24 for the lens basket assembly 23. The central aperture 48 is in intimate contact with the mounting plug 24 to provide a seal therebetween. In a preferred embodiment, the disc-shaped second liner section 46 is secured to the cap 16 via gluing, welding or other well-known securing method. Preferably the second liner section 46 is welded ultrasonically to the cap 16. The entire top surface or just the outer and inner edges of the second liner section 46 are secured such as by welding to the internal surface of the cap 16 so as to prevent any fluid passage from the inner space 22 between the second liner section 46 and the mounting plug 24.

Alternatively, the plug 24 into which the frame stem 28 inserts may be constructed of the same rigid porous material as the entire lid 16, with the underside surfaces of the plug covered with the second liner section 46, such as being coated with a silicone layer. For instance, FIG. 4 shows an alternative configuration for the leak-proof liner 42 wherein the mounting plug 24 is formed along with and of the same material as the rest of the cap 16, and where the second liner section 46 continues inward around all of the lower surfaces of mounting plug. This allows the basket stem 28 to be inserted into the plug 24 to form a completely sealed cap liner.

Still further, a lid 16 constructed entirely of silicone may be an option too, though silicones are typically not firm enough for that purpose. Thus, there could be a hard plastic outer threaded rim over which a silicone rubber "sheet" is fitted, with the silicone part also having a plug that serves to anchor the basket stem 28. Such a configuration would also reduce constraint on expansion of the silicone at higher pressure, thus providing greater pressure relief and/or greater visibility of the oxidative process working.

The material of the liner 42 is such that water is prevented from leaking out of the inner space 22. In a preferred embodiment, the liner 42 is formed of a silicone material that is highly oxygen-permeable yet water-impermeable even when a pressure in the inner space 22 exceeds an external pressure so as to permit oxygen to permeate through the liner. At the same time, the material of the rigid shell 12 is relatively porous to oxygen, such as a porous polyethylene, which therefore allows the oxygen that permeates through the liner to escape to the atmosphere. In the preferred material, i.e., non-porous silicone rubber, there are no identifiable pores. The passage of $O_2$ (and some other gases) occurs purely by being solubilized into the polymer from one surface and emitted from the polymer at the opposite surface. The flow of gas is driven by the $O_2$ concentration difference on the two sides of the polymer layer, and $O_2$ "dissolves" into the material and moves therethrough due to the concentration gradient. Thus, as $O_2$ concentration and pressure increase during peroxide neutralization, the flow of $O_2$ is from the inside to outside surface of the silicone liner, allowing eventual equilibration to near-atmospheric pressure inside the lens case. This is not the same as migration through pores in a membrane, as with earlier so-called "water-impermeable" materials such as GoreTex®, available from W. L. Gore & Associates, Inc., Newark, Del.

FIG. 3A is a depiction of the venting process whereby oxygen bubbles generated within the inner space 22 are forced against the inner liner 42; the first liner section 44 in this case. Dashed arrows through the first liner section 44 indicate the transit of oxygen through the liner due to its oxygen transmissibility or permeability. In other words, oxygen is soluble in the material of the liner 42. However, the liner material is completely nonporous and non-permeable or has near zero permeability to water molecules, so only oxygen escapes through it. The oxygen then passes easily through the outer shell 12 due to its porosity, as indicated by the rightward arrows.

One particularly suitable material for the liner 42 is a silicone rubber or siloxane that is hydrophobic and has high oxygen permeability. Some materials are purportedly non-permeable to water, such as polytetrafluoroethylenes (PTFE) having pore size between 0.01 μm to 100 μm (i.e., Gore-tex®), but in practice these materials leak water under pressure and have proven less than optimum for use as contact lens containers.

In the illustrated embodiment, the cap 16 includes at least one aperture 50 extending through the circular top wall 17. FIG. 1 shows three such apertures, though more or less may be provided. It should be noted that the second liner section 46 may be secured to the underside of the cap 16 at locations only around the mounting plug 24 and around the apertures 50, such as with welds.

To use the container 10 of the present invention, the lens holding basket assembly 23 receives contact lenses that are held in place by the opposed lens covers 32. A hydrogen peroxide sterilizing solution as described is then poured into the open end of the container 10. The cap 16 is then attached to the container. As the hydrogen peroxide decomposes into water and oxygen, the oxygen will transit through the oxygen-permeable, liquid-impermeable liner 42 and through the porous outer shell 12, as described above, or through one of the apertures 50. Under ambient conditions, water will not leak through the liner 42 or through the welds which bond the second liner section 46 to the cap 16. As provided above, a catalyst may be provided before or after the hydrogen peroxide sterilizing solution has been added and the lenses disinfected to destroy any residual hydrogen peroxide.

FIG. 4 also shows regions 52 of the second liner section 46 that flex outward into or through the apertures 50 from the internal pressure. These bubbles of liner 42 material are visible from above, and thus indicate to the user that the disinfectant process is working. Markings on the outer surface of the regions 52 may enhance the visibility, such as geometric shapes that deform when the regions bow outward or alphanumeric characters that enlarge. Additionally, the apertures 50 also serve as a safety valve of sorts to accommodate any increase in neutralization rate that might occur for any reason.

Figure 5:
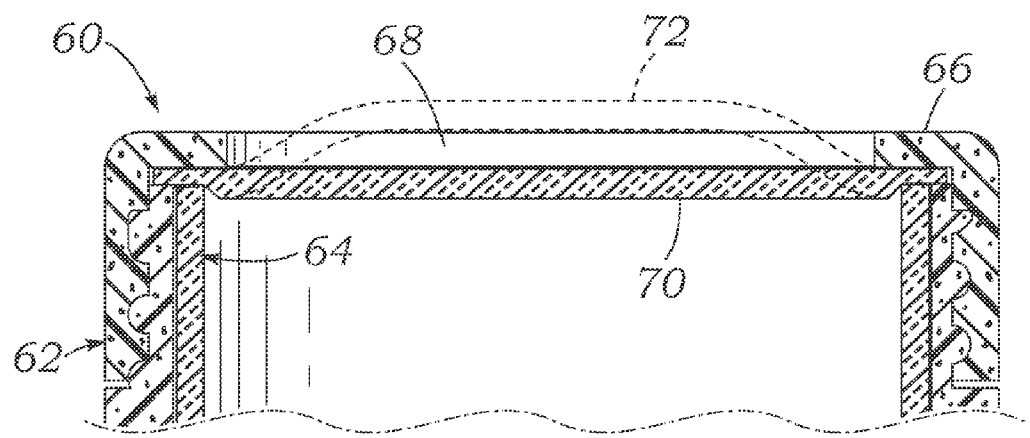
FIG. 5 is a detailed sectional view an upper end of an alternative container of the present application much like the embodiment of FIG. 3 with a leak-proof inner liner and rigid porous outer shell.

FIG. 5 shows another configuration of lens container 60 having a rigid, porous outer shell 62 and an inner water-permeable, oxygen-soluble liner 64. A cap 66 has a large orifice 68 in the top center that allows an inner liner 70 bonded under the cap to expand to the outside region of the cap when pressure accumulates inside the lens case, as seen in dashed line at 72. This bulging phenomenon supplies additional headspace for expansion of the gas (during the early part of neutralization, when oxygen is released at the highest rate, and thus reduces the maximum pressure that could occur during the neutralization process. This configuration may also serve as an indicator that the peroxide has reached a certain stage in the neutralization process and that oxygen has sufficiently been eliminated from inside the case. In this configuration no lens basket plug is provided in the cap 66, and thus a lens holding basket is simply placed into the inner space.

A still further configuration of container is to provide the cap structure shown in either FIG. 4 or 5, coupled with a water impermeable main body portion of the outer shell. That is, only the cap portion of the rigid outer shell will be porous, and the water impermeable liner contacting the open mouth of the main body so that all of the oxygen escapes through the cap. Of course, this lessens the capacity for pressure release, but providing a large surface area of oxygen-permeable liner under the cap may be enough.

Figure 6:
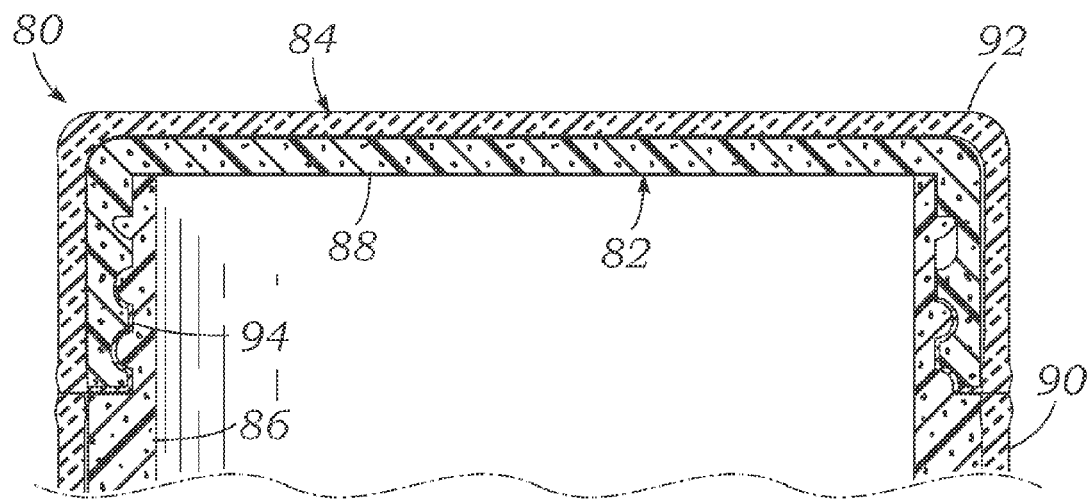
FIG. 6 is a detailed sectional view an upper end of another alternative container of the present application with a leak-proof outer liner and rigid porous inner shell.

Although the rigid, porous shell is conventionally used on the outside of the container, and the water-permeable, oxygen-soluble liner on the inside, it is also feasible to reverse the relative positions of these two elements. For instance, FIG. 6 illustrates a container 80 having an inner rigid porous shell 82 surrounded by a water-permeable, oxygen-soluble liner outer liner 84. The inner shell 82 includes a main body 86 having an upper open mouth onto which a cap 88 screws. The outer liner 84 includes a lower first section 90 coated or bonded to the outside of the main body 86 and an upper second section 92 coated or bonded to the outside of the cap 88. The first and second liner sections 90, 92 extend slightly beyond the main body 86 and cap 88 at their abutment so that they compress slightly together, as shown. Furthermore, a portion 94 of the second liner section 92 may extend inward on the cap 88 to a short way up the inner threading so as to ensure contact and a seal with the lower first liner section 90. The inwardly-extending liner portion 94 also functions as a locking mechanism in the final turn to insure airtight closure with no leakage even as pressure builds. This creates a complete liner 84 surrounding the space inside of the container to prevent water leakage. At the same time, oxygen passes easily through the porous inner shell 82 and then permeates through the outer liner 84. A section of the upper second section 92 of the liner 82 may be left unbonded to the cap 88 so that it bulges outward when the inside of the container becomes pressurized, thus providing an indicator of proper functioning.

Although not shown, the containers described herein could also incorporate a tablet dispensing mechanism in the cap so that multiple day in neutralization could be accomplished without the inconvenience of a separate neutralizer tablet package. That is, when an oxidative disinfectant is used, a reducing or neutralizing catalyst is preferable in an amount sufficient to chemically reduce or neutralize substantially all of the oxidative disinfectant. Therefore, for example, the separate mounting plug 24 illustrated in FIG.

3 may be provided with a dispenser to allow periodic introduction of a neutralizer tablet as needed.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims.

What is claimed is:

1. A contact lens sterilization container, comprising:
   a rigid outer shell including a main body and a cap removably attachable to an upper rim of the main body, the outer shell being porous to oxygen; and
   an inner liner including a first section covering the inner surfaces of the main body and a second section covering the inner surfaces of the cap in such a manner as to form a continuous barrier layer surrounding the inner space when the cap attaches to the main body, the inner liner and outer shell surrounding an inner space sized to receive one or more contact lenses, the inner liner being formed of a material that has high oxygen permeability yet is impermeable to water even when a pressure in the inner space exceeds an external pressure to permit oxygen to permeate through the inner liner and out the outer shell, wherein the first liner section comprises a layer adhered to the inside of the main body of the rigid outer shell which extends up to an upper rim, and the second liner section comprises a disc-shaped member adhered to the underside of the cap which has an outer perimeter wider than the upper rim of the first liner section such that the first and second liner sections come into intimate contact to form a seal when the cap attaches to the main body.

2. The container of claim 1, wherein the rigid outer shell is formed of a polyethylene, and the inner liner is formed of silicone.

3. The container of claim 1, wherein the cap of the rigid outer shell has at least one aperture formed therein under which the second liner section is positioned and the second liner section is formed of a flexible material such that when a pressure in the inner space exceeds an external pressure a portion of the second liner section flexes upward into the aperture as an indicator of the pressure differential.

4. The container of claim 3, wherein there is a single aperture formed in the cap extending substantially across the entire cap.

5. The container of claim 1, wherein the cap includes a downwardly depending mounting plug, and the container is provided with a lens-holding basket assembly that mates with the mounting plug to be suspended underneath the cap, and wherein the second liner section coats the entire undersurface of the cap including the mounting plug.

6. The container of claim 1, wherein the cap includes a downwardly depending mounting plug, and the container is provided with a lens-holding basket assembly that mates with the mounting plug to be suspended underneath the cap, and wherein the mounting plug comprises a separate element from the cap made of a water-impermeable material.

7. The container of claim 6, wherein the second liner section comprises an annular disc-shaped member having a central aperture that receives the mounting plug and is in intimate contact therewith.

8. A contact lens sterilization container, comprising:
   a rigid shell including a main body surrounding an inner space sized to receive one or more contact lenses, and a cap removably attachable to an upper rim of the main body, the shell being a porous polyethylene; and
   a liner including a first section disposed against the main body and a second section disposed against the cap in such a manner as to form a continuous barrier layer surrounding the inner space when the cap attaches to the main body, the liner being formed of a silicone material that has high oxygen permeability yet is impermeable to water even when a pressure in the inner space exceeds an external pressure to permit oxygen to permeate through the silicone liner and out the porous polyethylene shell, wherein the rigid shell comprises an outer member and the liner comprises an inner member, and the liner includes a first liner section adhered to the inside of the main body of the rigid outer shell which extends up to an upper rim, and the liner further includes a disc-shaped second liner section adhered to the underside of the cap which has an outer perimeter wider than the upper rim of the first liner section such that the first and second liner sections come into intimate contact to form a seal when the cap attaches to the main body.

9. The container of claim 8, wherein the cap of the rigid outer shell has at least one aperture formed therein under which the second liner section is positioned and the second liner section is formed of a flexible material such that when a pressure in the inner space exceeds an external pressure a portion of the second liner section flexes upward into the aperture as an indicator of the pressure differential.

10. The container of claim 8, wherein the cap includes a downwardly depending mounting plug, and the container is provided with a lens-holding basket assembly that mates with the mounting plug to be suspended underneath the cap, and wherein the second liner section coats the entire undersurface of the cap including the mounting plug.

11. The container of claim 8, wherein the cap includes a downwardly depending mounting plug, and the container is provided with a lens-holding basket assembly that mates with the mounting plug to be suspended underneath the cap, and wherein the mounting plug comprises a separate element from the cap made of a water-impermeable material.

12. A contact lens sterilization container, comprising:
    a rigid outer shell including a main body surrounding an inner space sized to receive one or more contact lenses, and a cap removably attachable to an upper rim of the main body, the cap being porous to oxygen; and
    an inner liner covering the inner surface of the cap in such a manner as to form a continuous barrier layer over the upper rim of the main body when the cap attaches to the main body, the inner liner being formed of a silicone material that has high oxygen permeability yet is impermeable to water even when a pressure in the inner space exceeds an external pressure to permit oxygen to permeate through the liner and out the cap's rigid porous outer structure;
    wherein the cap of the rigid outer shell has at least one aperture formed therein under which the inner liner is positioned such that when a pressure in the inner space exceeds an external pressure a portion thereof flexes upward into the aperture as an indicator of the pressure differential, wherein the portion thereof that flexes upward into the aperture includes a marking that deforms or enlarges to indicate the pressure differential.

13. The container of claim 12, wherein the rigid outer shell is formed of a porous polyethylene, and the inner liner is formed of a nonporous silicone rubber.

14. The container of claim 12, wherein there is a single aperture formed in the cap extending substantially across the entire cap.

15. The container of claim 12, wherein the cap includes a downwardly depending mounting plug, and the container is provided with a lens-holding basket assembly that mates with the mounting plug to be suspended underneath the cap, and wherein the inner liner coats the entire undersurface of the cap including the mounting plug.

16. The container of claim 12, wherein the cap includes a downwardly depending mounting plug, and the container is provided with a lens-holding basket assembly that mates with the mounting plug to be suspended underneath the cap, and wherein the mounting plug comprises a separate element from the cap made of a water-impermeable material.

17. The container of claim 12, wherein the marking is a geometric shape that deforms when the portion thereof flexes upward into the aperture.

18. The container of claim 12, wherein the marking is an alphanumeric character that enlarges when the portion thereof flexes upward into the aperture.

* * * * *